(12) United States Patent
Stal

(10) Patent No.: US 12,121,264 B2
(45) Date of Patent: Oct. 22, 2024

(54) INTRAVAGINAL CONCEPTION ASSISTANCE DEVICE, KIT OF PARTS, AND METHOD FOR INCREASING THE CHANCES OF GETTING PREGNANT

(71) Applicant: Fridababy, LLC, Miami, FL (US)

(72) Inventor: Robert Sebastian Stal, Aerdenhout (NL)

(73) Assignee: Fridababy, LLC, Miami, FL (US)

(*) Notice: Subject to any disclaimer, the term of this patent is extended or adjusted under 35 U.S.C. 154(b) by 0 days.

(21) Appl. No.: 17/895,367

(22) Filed: Aug. 25, 2022

(65) Prior Publication Data

US 2022/0409241 A1    Dec. 29, 2022

Related U.S. Application Data

(63) Continuation of application No. 17/253,352, filed as application No. PCT/NL2019/050378 on Jun. 18, 2019, now Pat. No. 11,452,547.

(30) Foreign Application Priority Data

Jun. 19, 2018 (NL) .................................. 2021153
Sep. 3, 2018 (NL) .................................. 2021551

(51) Int. Cl.
*A61B 17/43* (2006.01)

(52) U.S. Cl.
CPC .................... *A61B 17/43* (2013.01)

(58) Field of Classification Search
CPC ..... A61B 17/425; A61B 17/43; A61B 17/435; A61D 19/00; A61D 19/02; A61D 19/027; A61D 19/04
See application file for complete search history.

(56) References Cited

U.S. PATENT DOCUMENTS

| | | | |
|---|---|---|---|
| 1,743,733 | A | 1/1930 | Spardel |
| 2,089,113 | A | 8/1937 | Chalmers |
| 2,855,932 | A | 10/1958 | Stubbs |
| 4,381,771 | A | 5/1983 | Gabbay |
| 5,857,959 | A | 1/1999 | La Vean et al. |
| 8,192,347 | B2 | 6/2012 | Bollinger |

(Continued)

FOREIGN PATENT DOCUMENTS

| | | |
|---|---|---|
| AU | 2015203110 B2 | 6/2015 |
| AU | 2016299891 A1 | 2/2018 |

(Continued)

OTHER PUBLICATIONS

International Search Report mailed Sep. 5, 2019 issued in corresponding International Patent Application No. PCT/NL2019/050378 (3 pgs.).

(Continued)

*Primary Examiner* — Samuel G Gilbert
(74) *Attorney, Agent, or Firm* — Seyfarth Shaw LLP

(57) ABSTRACT

An intravaginal conception assistance device for collecting and presenting ejaculate relatively close to a cervix. The device has a cup part for collecting the ejaculate present in a vaginal canal and presenting it relatively close to the cervix upon moving through the vaginal canal towards the cervix. The cup part is substantially invertible. The cup part can be brought from a first, substantially non-inverted state into a second, substantially inverted state in which the cup part has been folded substantially inside out. As a result, insertion of the cup part into the vaginal canal can be facilitated.

7 Claims, 5 Drawing Sheets

(56) References Cited

U.S. PATENT DOCUMENTS

| | | | |
|---|---|---|---|
| 9,770,263 B2 | 9/2017 | Kanner et al. | |
| 2006/0099026 A1* | 5/2006 | Griffon | A45D 40/00 |
| | | | 401/265 |
| 2012/0143001 A1 | 6/2012 | Case | |
| 2013/0310767 A1* | 11/2013 | Solar | A61M 25/0102 |
| | | | 604/247 |
| 2014/0012216 A1 | 1/2014 | Shaviv | |
| 2017/0189222 A1 | 7/2017 | Lin | |
| 2017/0367736 A1 | 12/2017 | Kanner et al. | |
| 2018/0014854 A1* | 1/2018 | Souther | A61B 17/43 |
| 2018/0028350 A1 | 2/2018 | Wilson et al. | |
| 2019/0336324 A1 | 11/2019 | Choo | |
| 2020/0015854 A1* | 1/2020 | Jacoby | A61B 17/425 |
| 2021/0177645 A1 | 6/2021 | Crafton | |

FOREIGN PATENT DOCUMENTS

| | | |
|---|---|---|
| CN | 201453343 U | 5/2010 |
| EP | 3470026 A1 | 4/2019 |
| ES | 1159785 U | 6/2016 |
| FR | 3039060 A1 | 1/2017 |
| GB | 418326 A | 10/1934 |
| KR | 10-2016-0109503 A | 9/2016 |
| KR | 10-1877169 B1 | 7/2018 |
| TW | 547375 U | 8/2017 |
| WO | 2010/135349 A2 | 11/2010 |
| WO | 2014/025404 A1 | 2/2014 |
| WO | 2017/205356 A1 | 11/2017 |
| WO | 2017/212094 A1 | 12/2017 |

OTHER PUBLICATIONS

Written Opinion of the International Searching Authority mailed Sep. 5, 2019 issued in corresponding International Patent Application No. PCT/NL2019/050378 (8 pgs.).

* cited by examiner

INTRAVAGINAL CONCEPTION ASSISTANCE DEVICE, KIT OF PARTS, AND METHOD FOR INCREASING THE CHANCES OF GETTING PREGNANT

CROSS REFERENCE TO RELATED APPLICATIONS

This application is a continuation of U.S. patent application Ser. No. 17/253,352, filed Dec. 17, 2020, which is the U.S. National Stage of PCT/NL2019/050378, filed Jun. 18, 2019, which claims priority to: Netherlands Patent Application No. 2021153, filed Jun. 19, 2018, and Netherlands Patent Application No. 2021551, filed Sep. 3, 2018, the entire contents of each of which are herein incorporated by reference in their entireties.

FIELD

The invention relates to intravaginal conception assistance devices, or so-called intravaginal fertility devices or so-called intravaginal conception assistance devices, for collecting and presenting ejaculate relatively close to a cervix, wherein said device comprises a cup part for collecting the ejaculate present in a vaginal canal and presenting it relatively close to the cervix upon moving through the vaginal canal towards the cervix. Such a device can be used to improve fertility among couples after sexual intercourse, for instance as it may counteract backflow of spermatozoa from the cervix into the vagina. Additionally, it may prolong a time interval for spermatozoa to penetrate cervical mucus.

BACKGROUND

Such devices are for instance known from United States patent application publication US 2018/0014854 A1, which, amongst others, discloses an embodiment of an intravaginal device which comprises a cup part which is formed as a round, concave end cup. Said end cup is made of an elastically deformable material such that it to some extent can form to the shape of walls of a vaginal canal, when, after the end cup is inserted into the vagina after sexual intercourse resulting in ejaculation inside the vagina, the end cup is moved gently up the vaginal canal toward the cervix by pushing it inwards through the vaginal canal by means of a handle formed as a rigid shaft of about 20 cm long, which is attached to a bottom region of the end cup. Thanks to the end cup's elastically deformable side wall which may flex inwards to some extent, upon traveling through the vaginal canal, the end cup of the device may stay in contact with the walls of the vaginal canal relatively well, such as to facilitate the end cup in collecting ejaculate and subsequently presenting said collected ejaculate to an external orifice or so-called os of the cervix. The handle, which sticks out of the vagina after the end cup is pushed all the way up to the cervix, is also for pulling the device out of the vagina after it has been left in the vagina for a desired period of time, for instance for ten minutes to several hours.

However, even although the rigid shaft may be covered with the elastically deformable material, it may be unpleasant for a female user to keep the device with the rigid shaft in her vagina for several hours. A rigid shaft may even cause trauma to vaginal walls, in particular at introduction of the device, as, in a natural position of the vagina, a vaginal anterior wall and a vaginal posterior wall may then be in contact with each other substantially without leaving a space therebetween. Besides, the rigid shaft may prevent the female user from continuing her normal routine until the device is removed.

A disadvantage of such presently known device may lie in that it may be relatively unpleasant, if not painful, to insert the device, in particular when the female user cannot easily relax her pelvic floor muscles. Actually, the device may even cause trauma to vaginal walls, in particular at introduction of the device, as a vaginal anterior wall and a vaginal posterior wall may then be in contact with each other substantially without leaving a space therebetween in a natural position of the vagina. Further, it is noted that, for instance due to the size of the device, said device may be intimidating by look. Not only the female user may feel intimidated or scared by the device, but, additionally or alternatively, also her male partner may feel intimidated, for instance by the size of the device. This may not only make people completely refrain from using the device, but may, in case the device is actually used, lead to discomfort, lack of enjoyment and/or stress, for instance stress experienced due to pressure of having sex at the right moments within an ovulation window. This can be a huge disadvantage, as comfort can be very important, for instance because romantic sex and/or a female orgasm can be a factor substantially improving chances of getting pregnant.

SUMMARY

It is an object of the present disclosure to provide an alternative conception assistance device or so-called conception aid, which can be used to facilitate increasing chances of conception. In particular, it can be an object of the present disclosure to provide an alternative intravaginal conception assistance device, especially an alternative intravaginal conception assistance device for collecting and presenting ejaculate relatively close to a cervix, wherein at least one of the disadvantages of the prior art intravaginal conception assistance devices is counteracted. More in particular, the present disclosure may aim to provide an intravaginal conception assistance device, wherein at least one of the disadvantages mentioned above is counteracted. In embodiments, the present disclosure aims at providing an intravaginal conception assistance device, which can be used to collect ejaculate in a vagina and present the ejaculate relatively close to the cervix, and which on the one hand may be relatively non-intimidating, whereas it on the other hand may facilitate a relatively easy and/or relatively convenient and/or relatively controlled and/or relatively accurate positioning of a cup part of the device at or near an os of the cervix.

Thereto, the present disclosure provides for an intravaginal conception assistance device for collecting and presenting ejaculate relatively close to a cervix, comprising a cup part for collecting the ejaculate present in a vaginal canal and presenting it relatively close to the cervix upon moving through the vaginal canal towards the cervix, wherein said cup part is substantially invertible.

By making said cup part substantially invertible, the cup part can be brought from a first state into a second state in which the cup part has been folded substantially inside out, and vice versa. As a result, for example insertion of the cup part into the vaginal canal can be facilitated, for instance because a distal end edge of the cup part, which can be folded down in the cup part's second, substantially inverted state, is not to be inserted in the vagina first. Hence, insertion can be made relatively convenient, and/or pain sensation and/or trauma to vaginal tissue, for instance of the vaginal wall, can be counteracted. On the other hand, the first state may facilitate a relatively convenient and/or painless removal of the device.

It is noted that the first state may advantageously correspond with an initial state of the cup part, which also can be an initial state of the device. Said initial state, or so-called original state, may for example be a so-called natural state or substantially unbiased state, in which the cup part is when it is not distorted.

However, in alternative embodiments, the second state may correspond with the initial state and/or with a so-called natural state or substantially unbiased state of the cup part. The cup part may then initially be in its substantially inverted state in which it is substantially inside out, and may be substantially reinverted in order to bring it to a state in which it is no longer substantially inside out.

By providing the device with a handling element, in particular an elongate handling element, which may be attached to a bottom region of the cup part, it can be facilitated that a user of the device can pull the cup part from its second, substantially inverted state towards its first state, which thus may be its initial state, after the cup part has been inserted into the vagina. Additionally or alternatively, said handling element may also be suitable for removing the intravaginal conception assistance device from the vagina.

Although a user may pull the cup part from its substantially inverted state towards its substantially non-inverted state or so-called first state in order to turn it from said substantially inverted state towards said substantially non-inverted state, in embodiments, the cup part may naturally flip back to its substantially non-inverted state or so-called first state, in particular substantially without a user pulling at the cup part. The cup part may then for instance be biased towards said first state or substantially non-inverted state, such that, after it has been resiliently deformed into its substantially inverted state it can flip back or spring back substantially towards its original state.

By providing a distal end region of the cup part's side wall with a reinforcement or so-called fortification, the distal end edge of the cup part, which may be a substantially circular distal end edge, can keep its form, such as for instance a substantially circular form, relatively well when the cup part is substantially inverted, in particular substantially reinverted, from its second, substantially inverted state towards its first state, which preferably can be its initial state. By keeping its form relatively well, it can be facilitated that the distal end edge of the cup part stays substantially in place when the cup part is pulled, in particular pulled back, to its second state. The reinforcement, which may be formed as a local thickening at or near the cup part's distal end edge, may thus counteract that the cup part is unintentionally pulled back towards the posterior end of the vaginal canal instead of being substantially reinverted inside said vaginal canal.

By arranging the cup part such that it has a height which is smaller than its width, it can for instance be facilitated that the cup part can be substantially inverted relatively well. In particular, in the first state of the cup part, which preferably is the natural state of the cup part, the cup part itself and/or a main interior space defined by said cup part may have a height of at most 150% of its width, such as about half the size of the width. In embodiments, the cup part may be a substantially dome-shaped cup part, especially having a substantially hemispherical shape. However, in embodiments, the cup part may have any other suitable shape, such as for instance a substantially cone shape.

By providing a side wall of the cup part, in particular a side wall's portion located at or near the bottom region of the cup part, with at least one indentation defining a recess for a finger tip, it may be facilitated that the cup part can be handled relatively well. For example, the one or more indentations each defining a respective finger tip recess may facilitate checking whether the cup part has substantially turned, in particular substantially returned, to its first state. Additionally or alternatively, providing at least one indentation, and preferably at least two indentations, can also aid in removing the device, for instance because the indentation(s) can give an easy way to collapse the cup part to certain extent and/or to fold the cup part laterally over itself to at least some extent, which may help to remove the cup part from the ectocervix, thereby facilitating a relatively comfortable removal. Additionally, or alternatively, since the at least one indentation, and preferably at least two indentations, may facilitate that the cup part can be handled relatively well, said one or more indentations may help aid positioning the cup part, in particular positioning it substantially about the ectocervix. In particular in case the wall thickness, at least at the location of the one or more indentations, is relatively thin and/or in case at least the local region of the side wall of the cup part is relatively flexible, a user may feel relatively much through the cup part at the location of such indentation, which may help positioning the cup, for example in order to locate the ectocervix.

It is noted that, when the cup part is provided with one or more of such indentations, said one or more indentations may enable insertion of said device into the user's vagina with the use of one or two fingers by the user herself and pushing up the device between the vaginal walls up to the ectocervix, while the user can smoothly control and guide the insertion of the device by direct perception from the one or two inserting fingers, thereby counteracting pain sensation and/or trauma to vaginal tissue, which for instance is in contrast to prior art devices with a stiff shaft that is to be more or less blindly inserted into the vagina.

Advantageously, the conception assistance device can be provided in a kit of parts, which for instance also may comprise semen friendly moisturizer. For instance, the semen friendly moisturizer may be contained within a container. Alternatively, or additionally, at least a part of the conception assistance device may be pre-covered at least partly by semen friendly moisturizer. For example, the semen friendly moisturizer may be pre-applied to at least a part of the interior of the cup part, and may for instance be provided on an inner surface of the side wall of the cup part. Additionally or alternatively, semen friendly moisturizer may be provided in an optional reservoir which may be provided at a bottom section of a main interior space defined by the cup part. Additionally or alternatively, for instance at least a part of an outer surface of the side wall may be covered with pre-applied semen friendly moisturizer.

During use, the moisturizer may moisturize one or multiple parts of a female reproductive system, in particular it may moisturize the os of the cervix, thereby for instance softening or moisturizing the mucus present at the os of the cervix, by means of osmosis. As a result of a relatively high water content in the moisturized cervical mucus, the cervical mucus can be relatively accessible or penetrable to spermatozoa. Hence, spermatozoa may be facilitated to enter the cervix, and thereby the moisturizer can thus facilitate increasing the chances of getting pregnant.

Additionally or alternatively, the semen friendly moisturizer may form a semen friendly lubricant, may facilitate inserting the substantially inverted cup part into the vagina and/or may facilitate movement of the cup part through the vaginal canal. For instance thereto, said semen friendly moisturizer may for instance be applied at least to an inner surface of the side wall of the substantially invertible cup part, which inner surface will face substantially outwards when the cup part has been brought into its substantially inverted state. Alternatively or additionally, the moisturizer, which thus may form a lubricant, can be applied to the female and/or male genitals prior and/or during sexual intercourse.

Alternatively or additionally, the semen friendly moisturizer, which may thus also form a semen friendly lubricant, may facilitate that an environment to which spermatozoa are exposed inside the vagina may become less hostile or harsh for spermatozoa, for instance by making the environment less acidic, i.e. making the vaginal environment more semen friendly by increasing the pH, as a result of which the moisturizer may thus facilitate increasing the chances of getting pregnant.

The present disclosure also relates to a method for increasing the chances of getting pregnant. Said method comprises the steps of providing an intravaginal conception assistance device having a cup part which is substantially invertible; inserting the substantially invertible cup part into the vagina when said cup part is substantially in its substantially inverted state; moving the cup part through the vaginal canal towards the cervix, preferably thereby collecting at least a portion of the ejaculate; and substantially reinverting the substantially inverted cup part inside the vaginal canal.

Preferably, the method may be used to provide ejaculate relatively close to the cervix, in particular relatively close to the os of the cervix. It will be appreciated that the method may also provide a step of providing ejaculate in a vaginal canal of a vagina, for instance prior to, or alternatively at least partly simultaneous with, the step of inserting the cup part into the vagina.

The ejaculate can be provided in the vaginal canal prior to inserting the cup part into the vagina, more preferably the ejaculate can be provided in the vaginal canal by means of an ejaculation resulting from sexual intercourse. The device can then thus be inserted after sex. While moving the cup part through the vaginal canal, the cup part may then collect at least a portion of the ejaculate already present in said vaginal canal.

In alternative embodiments of the method, the ejaculate may for example be inserted into the vagina substantially simultaneously with inserting the device. For example, prior to placing the device, the ejaculate, for instance together with semen friendly moisturizer, may be put into the cup part, for instance at least partly in a reservoir, if any. Besides, as another example, the ejaculate may be inserted into the cup part after the cup part has been placed into the vagina, for instance at or near the ectocervix. For example thereto, the cup part may be provided with an opening or passage for inserting the ejaculate. For example, the passage may be formed as a canal extending through a stem or shaft forming an elongate handling element. Said stem may thus be formed as a hollow stem for insemination. It will be appreciated that the opening or passage may be provided with a closure or valve, for instance a one way valve, which may counteract that ejaculate flows back, out of the cup part, after it has been inserted into the cup part.

After the cup part has been put in place, in particular at or near the ectocervix, more in particular substantially around the ectocervix, preferably in its reinverted state, said cup part may be kept there for a certain period of time, for example for tens of minutes or for several hours, before removing the cup part from the vagina. For example, the cup part can be substantially reinverted upon insertion such that the cup part can subsequently be kept substantially in its first, substantially non-inverted state within the vagina for some time such as to allow at least a part of spermatozoa to move into the cervix.

Since the cup part can thus be substantially reinverted before removing the device, the cup part can be substantially tapering or narrowing in a downward direction, i.e. a direction away from the cervix, which may facilitate pulling down the cup part through the vaginal canal.

It is noted that, alternatively, or additionally, to presenting ejaculated to the cervix, the method may be used to present another substance to the cervix, in particular to the os of the cervix, such as for instance a moisturizer or a medicine.

In the method, the device may be used to moisturize one or multiple parts of a female reproductive system, in particular at least the os of the cervix. This may for instance be done prior to providing the ejaculate in the vagina, for example one or several days before ovulation and/or sexual intercourse to help moisturize cervical mucus, preparing it for conception. For instance, moisturizer, in particular semen friendly moisturizer, may be applied inside the cup part, e.g. within a main interior space or within a reservoir, if present. For example, a user may self apply the moisturizer or the moisturizer may for instance be pre-applied. After placing the cup part in the vagina, in particular at or near the ectocervix, more in particular in a manner substantially enclosing the ectocervix, said cup part may be kept there for a certain period of time such that the moisturizer can act upon for example the os of the cervix and/or mucus present at or near said os of the cervix. Although the semen friendly moisturizer can be inserted vaginally relatively long prior to intercourse, for instance one or several hours or even days prior to intercourse, additionally or alternatively the semen friendly moisturizer can be inserted vaginally relative shortly before intercourse, for instance within the last hours or minutes prior to penetration, for example such as to act like a semen friendly lubricant, and preferably as a moisturizer as well.

It is noted that the cup part is preferably inserted manually into the vagina, in particular by hand and without the use of any applicator. However, in alternative embodiments an applicator may be provided.

Advantageous embodiments according to the present disclosure are described in the appended claims.

BRIEF DESCRIPTION OF DRAWINGS

By way of non-limiting examples only, embodiments of the present disclosure will now be described with reference to the accompanying figures in which.

DETAILED DESCRIPTION

Figure 1:
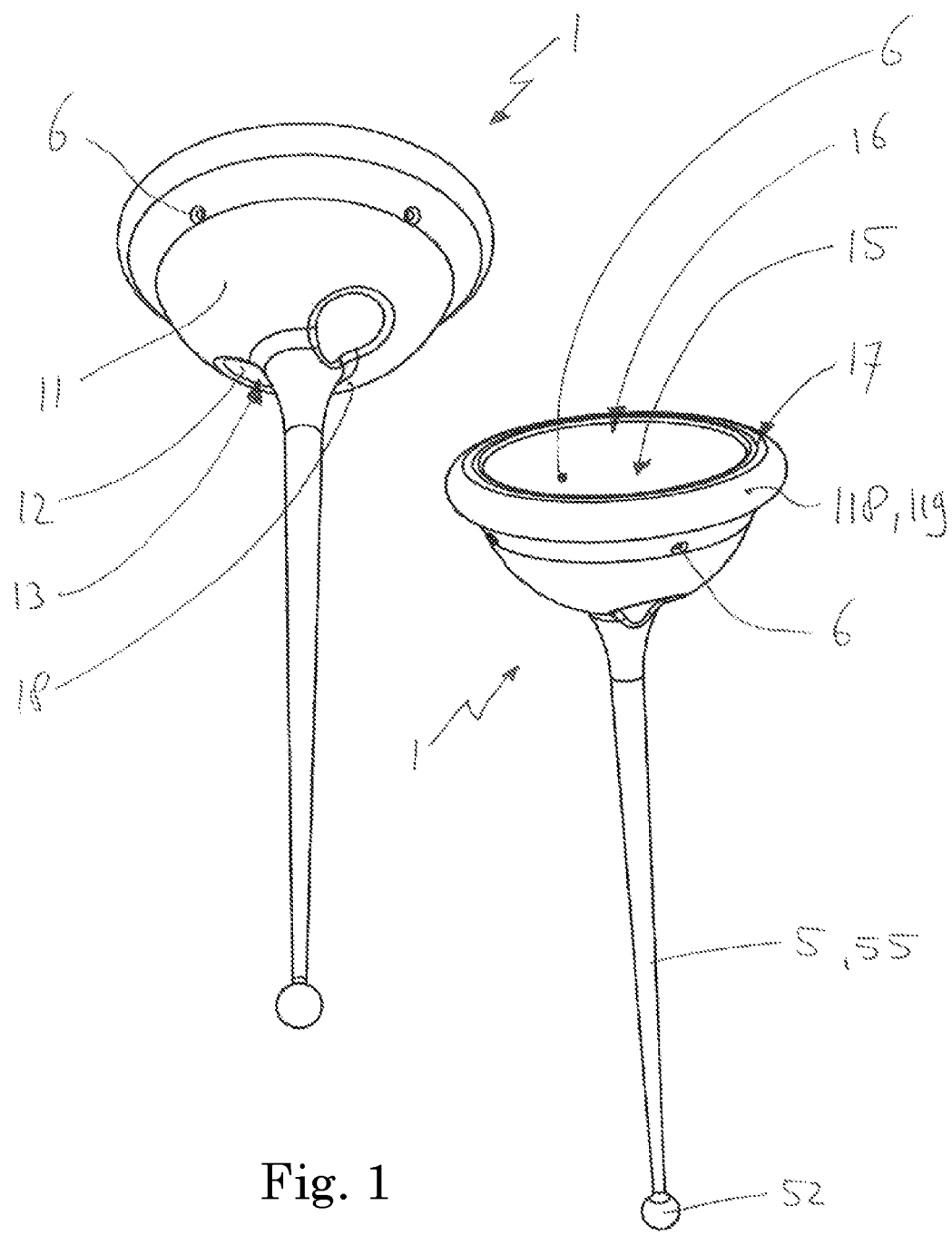
FIG. 1 shows a schematic perspective view of two identical intravaginal conception assistance devices according to an embodiment of the disclosure.

FIG. 1 shows an intravaginal conception assistance device 1 or a so-called fertility device 1. The intravaginal conception assistance device 1 is arranged for collecting and presenting ejaculate 2 relatively close to a cervix 3. The device 1 comprises a cup part 10 for collecting ejaculate 2 present in a vaginal canal 40 or so-called vaginal tract 40 or so-called vaginal cavity 40, for instance as a result of an ejaculation resulting from sexual intercourse. The cup part 10 is further arranged and intended for presenting the collected ejaculate 2 relatively close to the cervix 3 upon traveling through the vaginal canal 40 towards the cervix 3, the ejaculate thereby for instance bypassing the vaginal canal 40 relatively quickly, which may reduce the risk of spermatozoa being harmed by a relatively hostile, e.g. acidic, environment.

Figure 5:
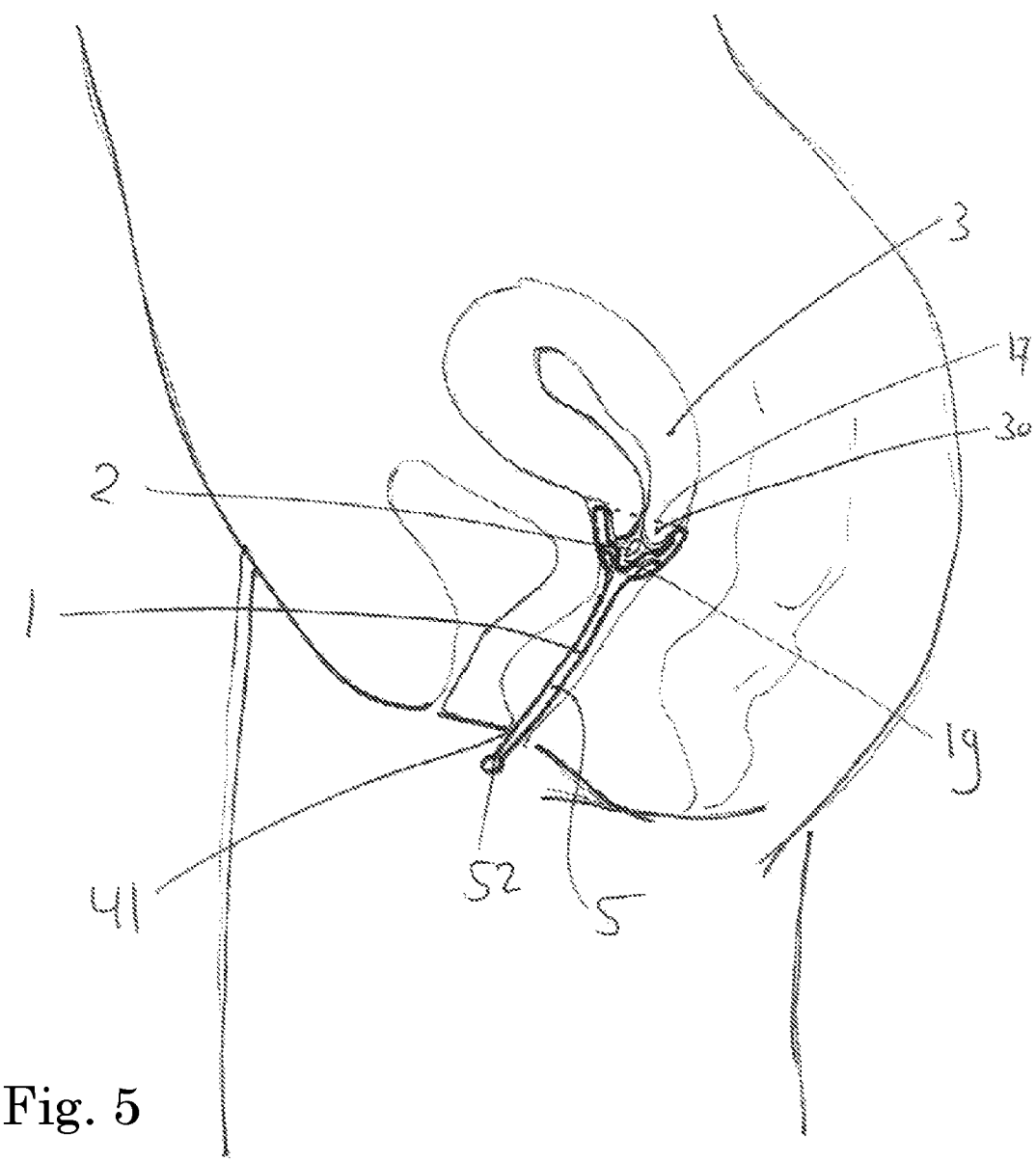
FIG. 5 shows a schematic cross-sectional view of the intravaginal conception assistance device positioned in the vagina.

It will be appreciated that the device 1 can be positioned in the vagina 4, with its cup part 10, or so-called cap part 10, positioned at a vaginal portion 30 of the cervix 3, also known as an ectocervix 30, as can be seen in FIG. 5, and that the ejaculate 2 can then be presented relatively close to the cervix 3. In particular, said cup part 10 can be located in a manner in which it substantially encircles the ectocervix 30. By keeping the cup part 10 positioned in that place for some time, for instance for a period of at least 10 minutes, preferably at least 1 hour, such as for instance for a period of 4 to 6 hours, or up to 8 hours or even longer, such as up to 24 hours, the ectocervix 30 can be exposed to a relatively large number of spermatozoa for a relatively long time, for instance as it can be counteracted that the ejaculate moves towards the entrance 41 of the vagina 4, or even leaves the vagina 4 unintentionally, while the female user can nevertheless follow a substantially normal routine. Hence, a female user can for instance go to the toilet without worrying about the ejaculate flowing out of her vagina, and does thus not have to feel the need to throw her legs in the air for a relatively long period of time after finishing the sexual intercourse. The device 1 can thus provide an increased amount of comfort and can allow increased mobility, thereby allowing a user to relatively freely move around and even go to work while wearing the device. It will be appreciated that by having the spermatozoa in place for a relatively long time, this may increase the chance the spermatozoa will be there at the right moment, e.g. during the fertile window. In particular, the device 1 may increase the fertile window by allowing the spermatozoa to be presented to the cervix in a relatively protected environment for extended periods of time. This may for instance allow a couple to have sex relatively long prior to the ovulation, which for instance may be advantageous if things like travel would otherwise get in the way of having sexual intercourse. An additional or alternative benefit may be that the cup part 10 can facilitate that the ejaculate 2 does not exit the vagina 4 in an inopportune time, for example when the user is at work. Additionally or alternatively, the ejaculate 2 may be relatively well protected by the device 1, especially as the ejaculate 2 in the cup part 10 can be substantially screened off from hostile, in particular relatively acidic, fluids present in the vaginal cavity 40.

It is noted that the female user in whose vagina 4 the device 1 is to be placed, may be the user whom may place the device 1. However, the device 1 may also be placed inside a female user's vagina by another user, for example a partner, in particular a male partner, of the female user, or by another user, for example a nurse, a doctor or other medical specialist. Although the device 1 can be suitable for home use, in a private and personal sphere, the device 1 may also be used in a medical environment and/or may be used under the supervision, and/or under the responsibility, of a medical specialist.

Figure 2:
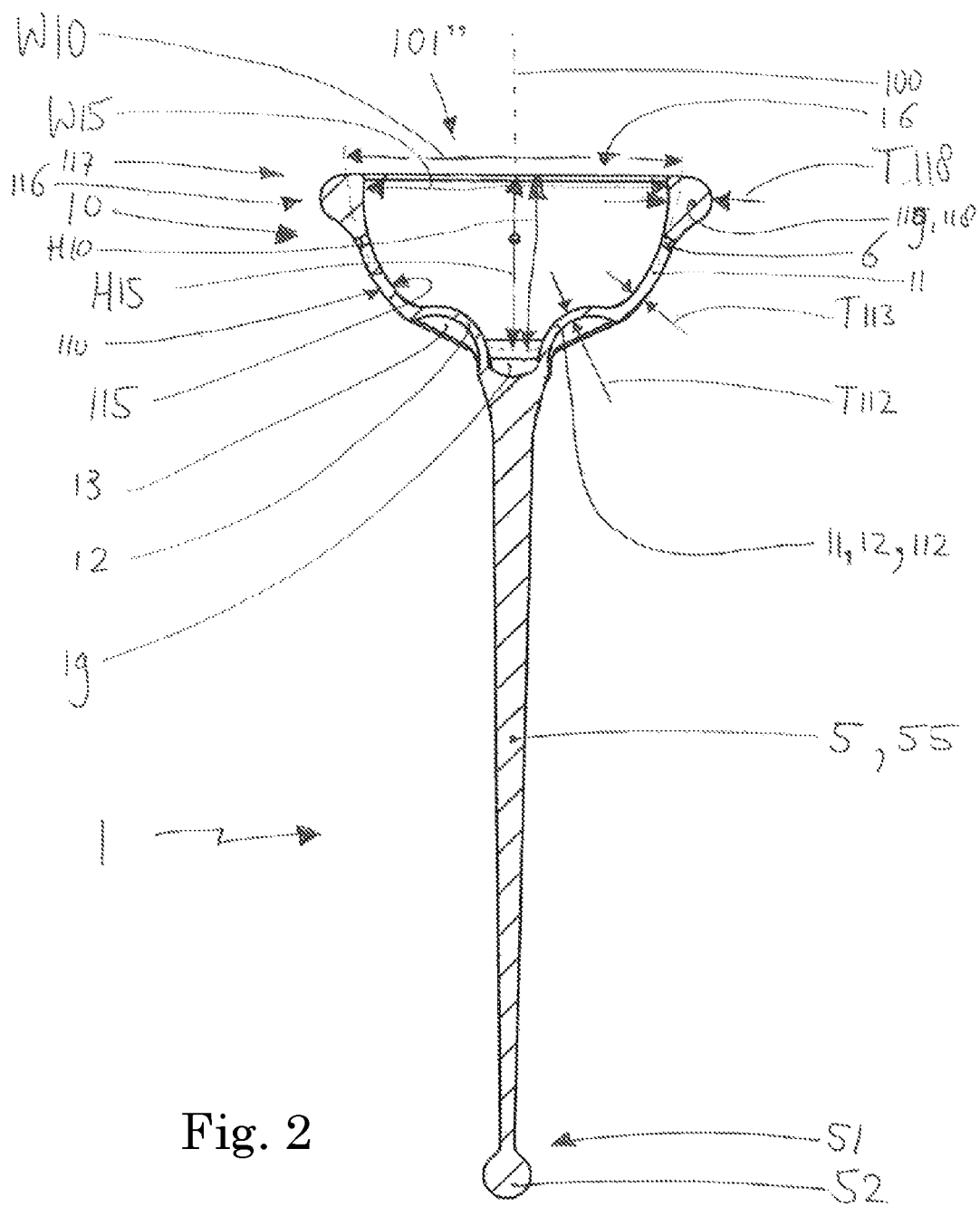
FIG. 2 shows a schematic cross-sectional view of the intravaginal conception assistance device of FIG. 1 in a first state.
Figure 3:
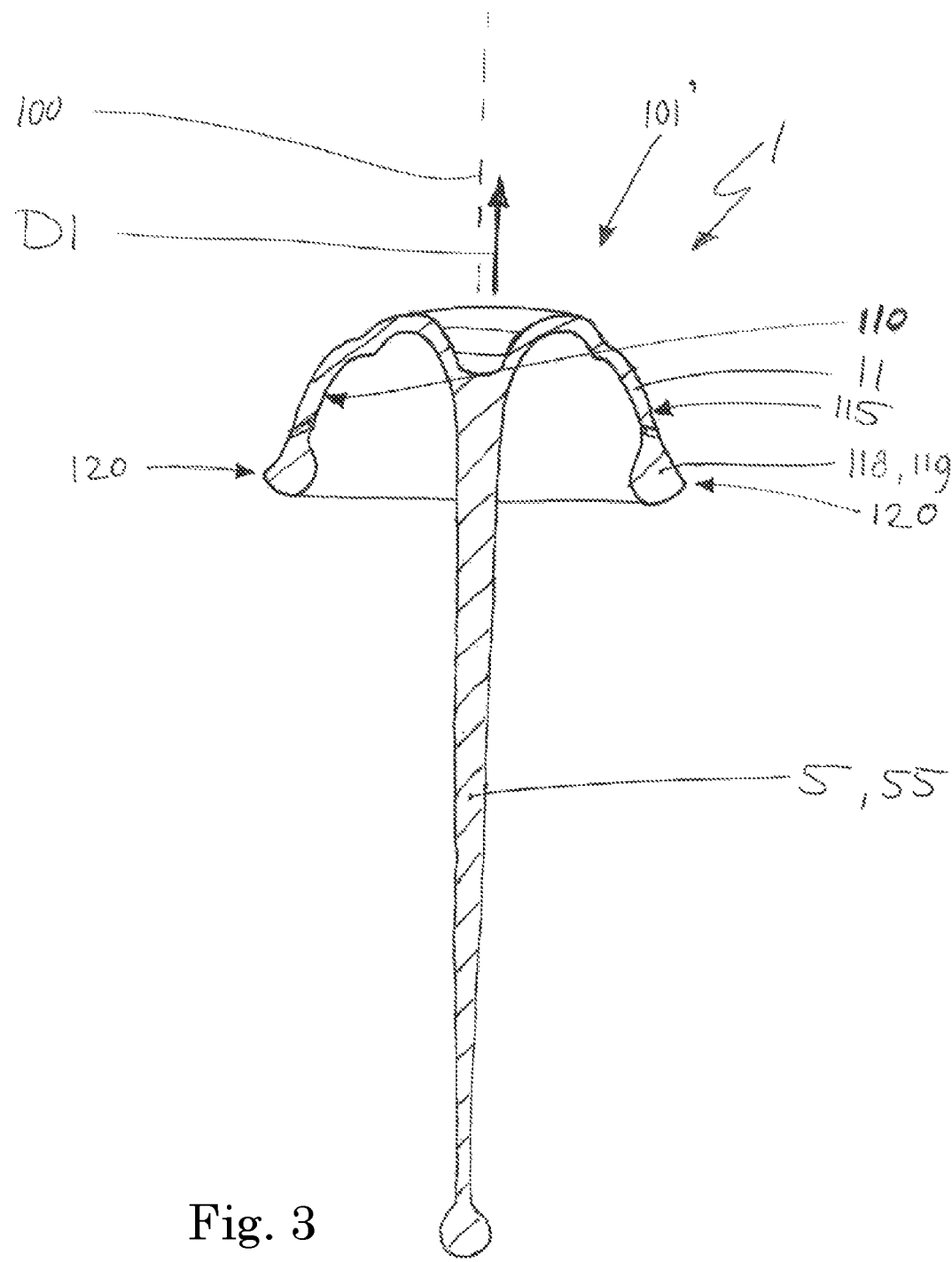
FIG. 3 shows a schematic cross-sectional view of the intravaginal conception assistance device of FIGS. 1 and 2 in a second state.

As for instance can be seen when comparing FIG. 2, which shows the device 1 with its cup part 10 in its first state, which preferably can be its initial state or natural state, with FIG. 3, which shows the device 1 with its cup part 10 in a second, substantially inverted or substantially reversed state, the cup part 10 is substantially invertible from the first state to the second state and vice versa. The device 1 is thus arranged for allowing that the cup part 10 can be brought from its first state, which preferably is its initial state, as is shown in FIG. 2, into a second state, as is shown in FIG. 3, in which the cup part 10 has been folded substantially inside out, in particular by simply flipping it inside out by hand. The cup part 10 can thus be folded over in a direction substantially along the central axial 100 of the cup part 10. A distal end edge 17 of the cup part 10 can thus be folded down in the cup part's substantially inverted state, as is shown in FIG. 3. As a result thereof, the cup part 10 may be substantially inverted or substantially reversed, in particular to such extent that in the second state the shape of the cup part 10 may be substantially an inverse shape of the shape of the cup part 10 in its first state. The distal end edge 17 has thus not to be inserted in the vagina 4 first, as a result of which insertion can be made relatively convenient, and/or pain sensation and/or trauma to vaginal tissue can be counteracted.

The cup part 10, which is substantially invertible, can be arranged to be invertible while inside the vagina 4. After insertion, the cup part 10 can thus be brought, in particular brought back, to its non-inverted state while inside the vagina 4. For example, the cup part 10, which may be substantially resiliently deformable, may be arranged to spring substantially back towards its non-inverted state. However, additionally or alternatively, a user may actively urge the cup part 10, while inside the vagina 4, towards the non-inverted state, for instance by pulling at a bottom section or bottom region 18 of the cup part 10, in particular while another section or region of the cup part 10, such as an end edge 17, is held substantially in place.

In particular, an, at least temporarily substantially outwardly facing, engagement means 120 of the cup part 10 can be held substantially in place, and may be substantially stopped and/or obstructed by the vaginal wall 42. Said engagement means 120, which for instance may include and/or may be formed by a ridge 120, may function as a barb or the like and may hold a local portion of the cup part's side wall 11, such as the end edge 17, substantially in place when the cup part 10 is substantially inverted towards its non-inverted state inside the vagina 4. Preferably, the engagement means 120 may be facing substantially outwardly in the inverted state of the cup part 10, while said engagement means 120 may be facing substantially inwardly in the non-inverted or first state of the cup part 10. In embodiments, the engagement means 120 may comprise a relatively sharp ridge 120, in particular a rounded off edge having a rounding off radius or edge radius of at most about 1 mm, preferably between 1 mm and 0.2 mm, such as about 0.5 mm. Additionally or alternatively other means for engaging the vaginal wall 42 may be provided, such as a relatively rough-texture, which may comprise little bulges or other protrusions, which may facilitate keeping the respective section or region of the cup part 10 substantially in place while said cup part 10 is pulled towards its substantially non-inverted state. It will be appreciated that the region or section provided with the engagement means may preferably be a region or section which may be reinforced such that it can keep in engagement with the vaginal wall 42 relatively well.

It is noted that, alternatively or additionally, the side wall 11 of the cup part 10, in particular at or near its distal edge, may be provided with scraping means 120, which for instance may be formed by such relatively sharp ridge 120, which in particular may be formed by a rounded off edge, more in particular one having a rounding off radius or edge radius of at most about 1 mm, preferably between 1 mm and 0.2 mm, such as about 0.5 mm. Such ridge 120 or other scraping means 120 may preferably face substantially outwards in at least the substantially inverted state of the cup part 10, such that said scraping means 120 can, when the cup part 10 is pushed through the vaginal canal 40 towards the cervix 3 in its substantially inverted state, scrape ejaculate from the vaginal wall 42, thereby for instance counteracting that relatively much ejaculate may not be collected, but for instance stay behind in folds or pits or the like present in the vaginal wall 42, which by nature is not very smooth. The scraping means 120 may thus facilitate that relatively much sperm can be brought relatively close to the os 31 of the cervix 3, thereby facilitating that relatively much sperm may reach the cervical mucus and/or enter the cervix 3, and thereby it may facilitate increasing a user's odds of conceiving.

As can be seen when comparing FIG. 3 with FIG. 2, the ridge 120, which in the substantially inverted state of the cup part 10 can face outwards may thus be relatively sharp with respect to the outwardly facing outermost face at the widest portion 116 of the cup part 10 being in its substantially non-inverted state. During insertion of the device 1, the relatively sharp ridge 120 may thus scrape relatively well, whereas the less sharp, relatively smooth face outwards when the cup part 10 is pulled back in the non-inverted state of said cup part 10 may facilitate that the cup part 10 can be pulled back towards the vagina entrance 41 in a relatively comfortable and/or gentle manner. It will be appreciated that although the ridge 120 forming the scraping means 120, which preferably can be made of silicone material which is relatively soft, may be relatively sharp with respect to said relatively smooth face facing outwardly in the non-inverted state of the cup part, said scraping ridge 120 may thus still be rounded to some extent such as to aid in a relatively comfortable insertion of the intravaginal conception assistance device 1.

As can be seen when comparing FIG. 3 with FIG. 2, the intravaginal conception assistance device 1 may be arranged such that the ridge 120 facing outwardly in the substantially inverted state of the cup part 10 can be relatively wide with respect to the substantially non-inverted cup part's widest width measured at the outer boundary of said substantially non-inverted cup part. As a result, the cup part 10 may thus be relatively wide during insertion, thereby for instance enabling that spermatozoa can be scraped towards the os 31 of the cervix 3 relatively well, whereas the cup part 10 may be somewhat narrower when it is pulled back towards the entrance 41 of the vagina 4, thereby for instance facilitating that the device 1 can be removed in relatively comfortable and/or gentle manner.

During removing the cup part 10, once the pulled back cup part 10 reaches the opening 41 of the vagina 4, the cup part 10 can be pinched, in particular by pressing two indentations 12 or so-called indents 12 towards each other and/or by folding the side wall 11 of the cup part 10 laterally over itself to some extent, in particular by performing a so-called C-fold. This may release a seal between the cup part 10 and the vagina 4, such that the cup part can be pulled out of the vagina 4 relatively gently.

Preferably, during its installation, the cup part 10 is first moved substantially up to the cervix 3 before it is being inverted to its substantially non-inverted state or before letting it flip back to said substantially non-inverted state. For instance due to that the vaginal canal 40 is relatively wide near the cervix 3, the cup part 10 may there then, after it has been brought in its substantially non-inverted state, be moved a little closer to the cervix 3, which before for instance was not be possible as the bottom of the cup part for instance was already abutting the ectocervix 30. It is noted that the cup part 10 may then, after being brought there substantially into its non-inverted state, be moved up a little further for instance by pushing said cup part 10 up or for instance as a result of that the cup part 10 more or less pops upwards automatically, in particular due to that a relatively wide end edge region of the cup part 10 is there, at the substantially diverging proximal end of the vaginal canal 40, more or less guided or urged by vaginal wall 42 towards a relatively wide portion of said vaginal canal relatively close to the cervix 3. After installation of the intravaginal conception assistance device 1, the cup part 10 may thus be accommodating the ectocervix 30 of the cervix 3 at least partly, for instance such as can be seen in FIG. 5. It is noted that the lower part or so-called base of the interior of the cup part 10 can then thus be positioned relatively close to the os 31 of the cervix 3, such that spermatozoa present in the ejaculate can be presented relatively close to the cervix 3, thereby increasing the changes that said spermatozoa reach the os 31 of the cervix, and thus increasing the changes that said spermatozoa can fertilize a female egg cell, or so-called ovum.

Advantageously, the intravaginal conception assistance device 1 can comprise a handling element 5. Said handling element 5 may be attached to a bottom region 18 or so-called bottom section 18 of the cup part 10. It is noted that the handling element 5 can be arranged for pulling the cup part 10 from its second, substantially inverted state towards its first state, while being inside the vagina 4. In particular, in case the first state is the initial state, the cup part 10 can then thus be pulled back towards its initial state. Said handling element 5 may also be suitable for facilitating removal of the intravaginal conception assistance device 1 from the vagina 4.

Preferably, the handling element 5 can be an elongate handling element, for instance having a length of at least 25 mm, in particular at least 5 cm, more in particular between 5 cm and 15 cm, yet more in particular between 6 cm and 10 cm, such as for instance about 8 cm.

In embodiments, the handling element 5 may be formed as a stem 55, in particular a substantially flexible stem 55. For example, said stem 55 may comprise a flexible, preferably elastically deformable, material, such as for instance a silicone material or a thermoplastic elastomer material, in particular medical grade silicone material or medical grade thermoplastic elastomer material.

Advantageously, substantially the entire outer surface of the device 1, or even substantially the entire device 1, may be made of relatively very soft material, such as for example a silicone material or a thermoplastic elastomer material. Additionally or alternatively, the device 1 may be free of any sharp protrusions and/or any sharp edges. In particular, the entire device 1, including all its edges, may be rounded for making its use relatively comfortable.

The stem 55, in particular a substantially flexible stem, can be rigid to some extend, such that said stem 55 may also be used to push the cup part 10 into position when positioning the device 1 in the vagina 4, in particular when pushing it through the vaginal canal 40. It will be appreciated by the skilled person that although the stem 55 may thus be substantially flexible, the cup part 10 may thus be arranged for and usable to transfer a pushing force.

Although the handling element 5 may in embodiments be formed by a stem 55, said handling element does, for instance in alternative embodiments, not need to be suitable for pushing the cup part 10 ahead. For example, in preferred embodiments, the handling element may comprise and/or may be substantially formed as a string or cord or the like, and may then for instance be arranged for pulling the cup part 10 from its second or substantially inverted state towards its first, substantially non-inverted state and/or for forming a removal element for removing the intravaginal conception device 1 from the vagina 4. Although, such flexible string, flexible cord or other flexible handling element 5, such as a tendril or the like, may substantially not be suitable for pushing the cup part 10 through the vagina 4, it may facilitate that the device 1 can be relatively comfortable to wear as it may be flexed, twined, bent or curled when the device 1 has been installed.

In embodiments, a proximal end 51 of the handling element 5 may be provided with a grip 52, in particular formed as a protrusion 52 or thickening, more in particular a substantially rounded protrusion or round knob 52, which may provide additional grip, for example when the substantially inverted cup part 10 is pulled towards its substantially non-inverted, first state or for example during removal of the cup part 10 from the vagina 4. Additionally or alternatively, in particular in case the handling element 5 is formed as a shaft or stem, such protrusion 52 or thickening 52 may counteract that the proximal end 51 may prick the user. However, it will be appreciated that the protrusion or other grip may be of another design, for instance being substantially flat and may additionally or alternatively comprise a finger hole or the like, and can for instance be formed as a ring or loop located at a proximal end of an elongate handling element 5 formed by a string or a cord or the like.

It is noted that, in the second, substantially reversed state of the cup part 10, the distal end 101' of the device 1, which then is temporarily formed by the substantially inverted cup part 10, may be substantially convex, as can be seen in FIG. 3, whereas the distal end 101" of the device 1 may be substantially concave when the cup part 10 is in its substantially non-inverted, first state, as can be seen in FIG. 2.

Figure 4:
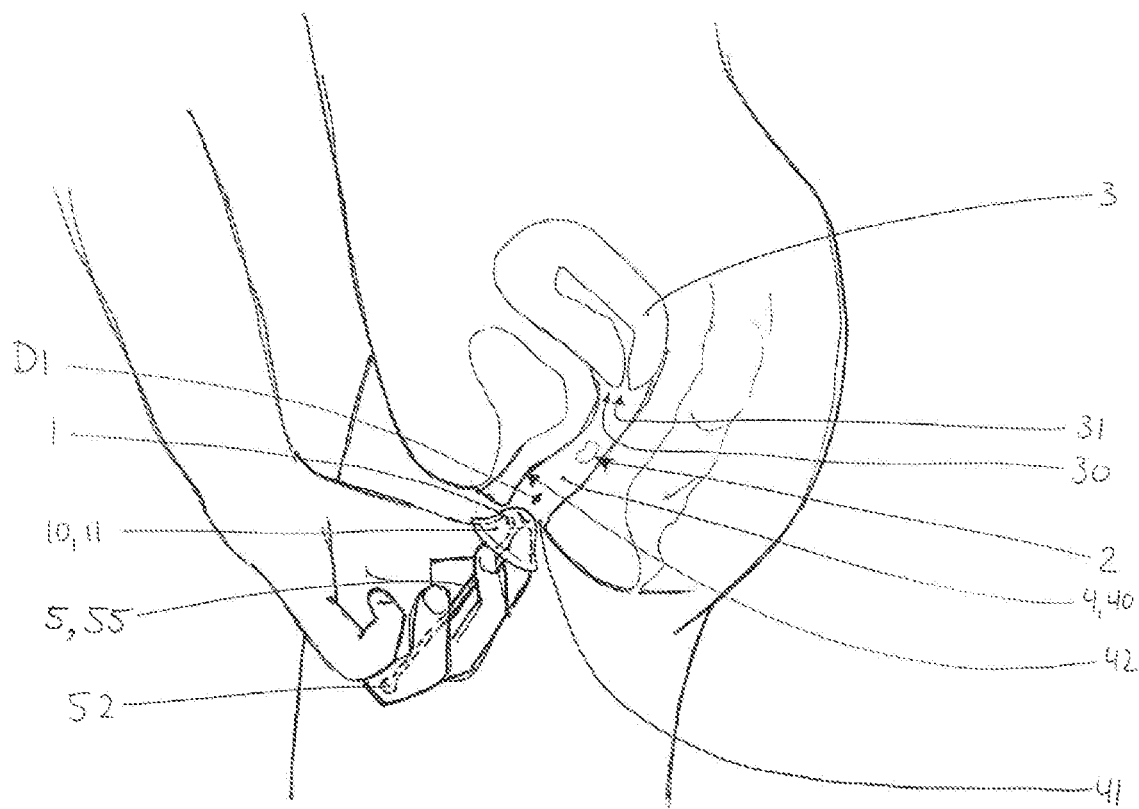
FIG. 4 shows a schematic view of an embodiment of said intravaginal conception assistance device during insertion into a vagina.

Actually, as can be seen in FIGS. 3 and 4, in the substantially reversed state of the cup part 10, said temporarily substantially inverted cup part 10 may substantially narrow or substantially taper in a direction which substantially corresponds with an inserting direction D1 in which the cup part 10 is to be inserted into the vagina 4.

In embodiments, the widest portion 116 of the cup part 10, may be located at or near the distal end 117 of the cup part 10, in particular within the uppermost 33% of the height H10 of the cup part 10, more in particular within the uppermost 25%, uppermost 20% or uppermost 15% of said height H10. By folding down the side wall 11 of the cup part 10, such as to fold the cup part 10 substantially inside out, said widest portion 116 may thus be moved temporarily to a lower location to such extent that said widest portion 116 temporarily is not any longer located at or near the distal end of the cup part 10 to be inserted, as can be seen when comparing FIG. 3 with FIG. 2, as a result of which insertion of the cup part 10 into the vaginal canal 40 can be facilitated.

During insertion of the cup part 10, a user may keep one or more finger tips inside the substantially inverted cup part 10, for instance in a manner corresponding to the situation shown in FIG. 4, and push the cup part 10 into the vagina 4. A cup part 10 which is folded inside out may thus cover one or more fingers during at least a portion of the insertion of the cup part 10. Nevertheless, the user may insert the cup part 10 in a different suitable manner, and may for instance hold one or more fingers on the outwardly facing surface 115 of the cup part 10, which may be the initial inside surface 115 of the cup part 10, for instance in order to counteract that the cup part 10 unintentionally flips towards its non-inverted state.

It is noted that although folding the cup part 10 substantially inside out may thus ease inserting the cup part 10, the cup part 10, prior to insertion, may for instance additionally be folded laterally over itself to at least some extent, for instance by pushing a portion of the side wall 11 laterally inwards towards the central axis 100, in particular such that, when seen from above, the substantially inverted cup part is then substantially C-shaped, such as to create a relatively small profile, which may ease insertion into an entrance 41 of the vagina 4. After insertion of the substantially inverted cup part 10 into the vagina 4, the cup part 10 may be substantially unfold laterally, and can subsequently, in particular when still being in its substantially inverted state, be pushed towards the cervix 3 while it collects the ejaculate 2, or so-called seminal fluid or semen, present in the vaginal canal 40.

In order to ease removal of the device 1, the cup part 10, which may then be in its first state, may also be folded laterally over itself to at least some extent, for instance by pushing a portion of the side wall 11 laterally inwards towards the central axis 100, for example such that, when seen from above, the cup part 10 then is substantially C-shaped, such as to create a relatively small profile, which may ease removing the device 1. It is noted that in embodiments in which one or more indentations 12, which may form a respective finger tip recess 13 for receiving and then lodging a respective finger tip at least partly, are provided, these one or more, preferably two, indentations 12 may facilitate a user to collapse the cup part 10, when placed inside the vagina 4 and substantially about the ectocervix 30, for example collapsing it substantially in a manner that the cup part 10 may be folded laterally over itself to some extent, e.g. forming a so-called C-fold.

It will be appreciated that at least a side wall 11 of the cup part 10 can be made of a flexible material, in particular an elastically or resiliently deformable, flexible material, such as for instance a silicone material or a thermoplastic elastomer material, or so-called TPE material, preferably medical grade silicone material or medical grade TPE material.

Further, it is noted that a wall thickness T113 of the side wall 11 of the cup part 10 may be relatively thin in order to facilitate that the cup part 10 can be substantially inverted or substantially folded inside out. For example, a ratio between said wall thickness T113 and the height H10 of the cup part 10 may be smaller than 1:6, preferably at most 1:8, for example at most 1:10 or at most 1:12.

It will be appreciated that the wall thickness T113 does not need to be the same over the entire side wall 11, and that one or more local portions of the side wall 11 may for instance have a smaller local wall thickness T112, for instance at the location of an indentation 12 defining a recess for a finger tip for facilitating handling of the device 1, and/or that one or more local portions of the side wall 11 may for instance have a larger local wall thickness T118, for instance at the location of a local thickening 118 for locally reinforcing the cup part 10.

As noted above, the side wall 11 of the cup part 10 may be provided with at least one indentation 12 defining a recess 13 for the finger tip, which may facilitate that the cup part 10 can be handled relatively well, and can for instance be installed in a relatively controlled and/or relatively accurate manner. The indentation(s) 12 can preferably be located in a portion of the side wall located at or near the bottom region of the cup part 10.

Advantageously, the side wall 11 of the cup part 10 is provided with at least two indentations 12, each defining a respective recess 13 for a respective finger tip, for instance one for a tip of an index finger and one for a tip of a middle finger, as a result of which it may for instance be facilitated that the cup part 10 can be guided and/or disposed relative well.

By providing multiple recess 13 defining indentations 12, it may for example be facilitated to control the cup part 10, especially when the user tries to locate the cup part 10 relatively accurately with respect to the ectocervix 30, for instance after the previously substantially inverted cup part has already been substantially reinverted by the user. For example at such relatively late stage of positioning the cup part 10, the user may have located a tip of an index finger in a first one of the recesses 13 and may have located a tip of a second finger, for instance a middle finger, in a second one of the recesses 13.

Alternatively or additionally, providing at least one indentation 12, and preferably at least two indentations 12, can also aid in removing said cup part 10, because it can give an easy way to fold the cup part 10 laterally over itself to at least some extent while still partially inside the vaginal canal 40, thereby facilitating a relatively comfortable removal.

By arranging the device 1 such that the side wall 11 of the cup part 10 has a relatively small local wall thickness T112 at the location of the at least one indentation 12 formed in said side wall 11, in particular a local wall thickness T112 being smaller than an adjacent local wall thickness T113 of a section of the side wall 11 adjacent to said at least one indentation 12, especially in case the material of the side wall 11 is a flexible material, it can be facilitated that the user inserting the cup part into the vagina can feel relatively much through the cup part 10. This may for instance facilitate locating ectocervix 30 and/or may facilitate positioning the cup part 10 relatively accurately with respect to the ectocervix 30, in particular relatively accurately about the ectocervix 30.

For example, the local wall thickness T112 at the location of the at least one indentation 12 can be less than 90%, preferably less than 80%, such as for instance less than 75% or less than 70% of the adjacent local wall thickness T113. Additionally, or alternatively, the local wall thickness T112 at the location of the indentation 12, i.e. a wall thickness T112 of a section 112 of the side wall 11 defining the recess 13, can preferably be at most 2 mm, more preferably at most 1.5 mm, such as about 1 mm, or even less. As the side wall 11, at least at the location 112 of said indentation 12, may be made from flexible material, in particular flexible silicone material or flexible thermoplastic elastomer (TPE) material, such a relatively thin thickness T112 may help the user to feel through the cup part 10 relatively well, e.g. in order to locate the ectocervix 30.

Besides, it is noted that, in advantageous embodiments, a region of the side wall 11 located at or near the distal end 117 of the cup part 10 may be provided with a reinforcement 119 for counteracting that the distal end edge 17 of the cup part 10 gets distorted relative much when the cup part 10 is substantially inverted, in particular substantially reinverted, from its second, substantially inverted state towards its first, substantially non-inverted state. The cup part's distal end edge 17, which may be substantially shaped as a loop, a circle, an oval or the like, may then thus substantially keep its shape when the cup part 10 is substantially reinverted inside the vagina 4, in particular upon reaching a proximal end region of the vagina canal 40 at or near the vaginal portion 30 of the cervix 3.

It is noted that the reinforcement 119 can in particular be located at a certain region of the side wall 11 of the cup part 10, in particular a substantially circumscribing region, which preferably is located at or near a distal end edge of the cup part 10, and which for instance can be substantially formed as a ring 118 located at or near the distal end 117 of the cup part 10, and that it may be relatively stiff. Such reinforcement, in particular substantially ring-shaped reinforcement, may, in particular when the cup part 10 has a certain minimal diameter or minimal width T118 at the location of said reinforcement 119, facilitate that the cup part 10 can be clamped within vagina 4 by the vaginal wall 42 to some extent, in particular such that a clamping force exerted by the vaginal wall may be of such magnitude that it can counteract that the cup part is pulled down inside the vagina 4 when one pulls the cup part 10 to its non-inverted state. For example, the cup part 10 can have a certain minimal outer width T118 or minimal outer diameter T118, in particular at or near an upper end 116 or upper edge 17 of the cup part 10, which may be at least 21 mm, in particular at least 25 mm or at least 30 mm, more in particular at least 35 mm or at least 38 mm, such as about 40 mm.

In embodiments, the reinforcement 119 or so-called fortification 119 may comprise a reinforcement material, which may be relatively stiff with respect to the material of the side wall. For example by means of insert moulding, said reinforcement material may be encased within a relatively flexible material, such as medical grade silicone material.

Alternatively, or additionally, the reinforcement 119 or so-called fortification 119 may for instance comprise a local thickening 118 of the side wall 11, in particular wherein said thickening 118 extends substantially along the perimeter of the cup part 10. As a result of the thickening, the side wall 11 of the cup part 10 may locally, in particular at or near its distal end edge, be relatively stiff or relatively rigid, as result of which said side wall 11 at the location of the thickening 118, 119 may be hardly deformable or only with difficulty. For example, the local thickening 118 can be substantially formed as a ring 118 located at or near the distal end 117 of the cup part 10. Said ring 118 may for instance have a local thickness T118 which is at least twice as large as the thickness T113 of a non-thickened portion of the side wall 11, preferably being at least three times as large.

With respect to the side wall thicknesses, it is noted that a respective side wall thickness T113, T118, T112 should be measured in a local direction substantially transverse to the side wall 11, as can be seen in FIG. 2.

In embodiments of the intravaginal conception assistance device 1, the cup part 10 can have a height H10 which is smaller than its width W10. As can be seen in FIG. 2, said width W10, at the widest point of the cup part 10, can for example be measured substantially from the local centre of the side wall 11 to the local centre of the side wall 11 positioned opposite thereto. Alternatively, said width W10, at the cup part's widest point, may be measured at its outer boundary.

It is noted that the cup part 10 can be a substantially dome-shaped cup part 10, especially having a substantially hemispherical shape, which, in embodiments, then for instance may be provided with a local thickening 118 and/or one or more indentations 12 and/or other deviations such as one or more protrusions, etc. For instance in case of a substantially hemispherical shape, the width W10 of the cup part 10 can be substantially twice as large as the height H10 of said cup part 10.

It is noted that the cup part 10, in particular its side wall 11, may define a main interior space 15 arranged and dimensioned for receiving the ectocervix 30 of the cervix 3 at least partly. The cup part 10, which can be considered a hollow cap 10, may have an opening 16, in particular an annular opening 16, defined by an upper edge 17 of the cup part 10, which can form a distal end edge 17 of the cup part 10. Preferably, said main interior space 15 may be substantially dome-shaped and/or substantially bell-shaped, and in particular it 15 may be of a substantially hemispherical shape, as is the case in the embodiment shown in FIGS. 1 and 2, and which may facilitate that the cup part 10 can be clamped onto the ectocervix 30 relatively well.

It is noted that, once installed, the cup part 10 may remain in place substantially about the ectocervix 30 for instance due to the cup part 10 being at least partly resiliently or elastically deformable, as a result of which the cup part 10 may clamp onto the ectocervix 30 to a certain extent. For instance, the upper end edge 17 of the cup part 10 may provide for a resilient ring 118, which may be relatively thick with respect to the wall thickness T113 of the side wall 11 of the cup part 10, as a result of which it may clamp relatively well. Additionally or alternatively, the cup part 10 may be kept in place at least to some extent due to the nature of the vagina 4, which may for instance clamp the cup part 10 inside it, and/or due to the shape of the vaginal canal 40, which at its proximal end located near the ectocervix 30 may taper to some extent in a downward direction, as can be seen in FIG. 4.

Preferably, the cup part 10 may be of such design that, in particular in its first state, as is shown in FIGS. 1 and 2, the width W15 of the main interior space 15 substantially decreases in a direction from the upper edge 17 towards a bottom section 18 of the cup part 10. In an upward direction, from the cup part's bottom section 18 towards the upper opening 16 of the cup part 10, the main interior space 15 may substantially widen, such as to facilitate receiving the ectocervix 30. In particular, due to such design of the main interior space 15, which can allow the interior space of the cup part 10 to be substantially filled up with the ectocervix 30 when the cup part 10 has been put in place, there may not be much room for a spermatozoon to swim around, thereby increasing the chances that the spermatozoon reaches the os or so-called external orifice 31 of the cervix 3.

At the bottom section 18 of the main interior space 15 defined by the cup part 10, a depression 19 can be provided that forms a reservoir 19 for semen and/or moisturizer, wherein, in the first state of the cup part 10, said reservoir 19 is located below the main interior space 15 and is in fluid connection with said main interior space 15. The volume of the reservoir 19 can be relatively small with respect to the volume of the main interior space 15. The reservoir 19, which may be substantially dome-shaped, may taper to some extent, in particular taper away from the distal end of the device 1 in a downward direction along the central axis 100 of the cup part 10.

The reservoir 19, in embodiments in which it is present, may present semen, moisturizer, and/or another substance to be presented to the os 31 of the cervix 3, relatively close to said os 31, and/or may counteract that a relatively large portion of such substance is pushed out of the cup part 10, e.g. pushed out by the ectocervix 30, upon positioning the cup part 10.

In embodiments, the main interior space 15, excluding the optional reservoir 19, can have a height H15 being smaller than its width W15 preferably being at most 150% of its width, such as about half the width W15. In particular, said width W15 may be considered the widest width W15 of the main interior space 15.

Said width W15 of the cup part's main interior space 15, which preferably may be located at or near the top edge 17 of the cup part 10, can be at least 21 mm, in particular at least 25 mm, more in particular at least 30 mm, such as about 31 mm or about 33 mm. On the other hand, the widest internal width W15 may also be limited to some extent, and may therefore for instance be at most 55 mm, in particular at most 45 mm, more in particular at most 40 mm or at most 35 mm, such as about 34 mm or about 32 mm.

Additionally or alternatively, the main interior space 15, in particular excluding the reservoir 19, if present, may have a height H15 of at most 40 mm or at most 35 mm, in particular at most 32 mm, more in particular at most 30 mm, such as at most 28 mm, such as about 25 mm, and/or wherein the height of the interior space is at least 10 mm, in particular at least 12 mm, more in particular at least 15 mm or at least 17 mm, such as about 20 mm or about 25 mm.

By making said height H15 relatively low, it can be facilitated that the cup part 10, when in its substantially reversed state, can be inserted into the vagina 4 relatively fast. Especially, due to said height H15 being relatively low, the height of the substantially inverted cup part 10 is relatively low, thereby enabling that the flipped over side wall 11 can be inserted into the vagina 4 via the vaginal opening 41 or so-called entrance 41 of the vagina 4 relatively fast, thereby counteracting that relatively much semen may flow out of the vagina 4, for instance by flowing over said flipped over side wall 11, when the substantially inverted cup part 10 is being pushed through said vaginal opening 41 between the labia.

Additionally or alternatively, by making said height H15 relatively low, it can be facilitated that the local thickening 118, such as the ring 18, or other distal portion of the cup part 10 which in the substantially non-inverted first state of the cup part 10 is located near its distal end 117, such as a distal end edge, may still be located relatively close to the device's distal end 101' when the cup part 10, in its substantially inverted second state, is pushed through the vagina 4 towards the cervix 3. When the device's distal end 101' abuts the ectocervix 30, said local thickening 118 and/or the distal end edge is thus delivered to a position relatively close to said ectocervix 30, and the cup part 10 can thus be reinverted at relatively nearby the cervix 10, thereby facilitating that the cup part 10 may be installed relatively well around the ectocervix 30.

In embodiments, the main interior space 15, excluding the reservoir 19, if any, may have a volume of at least 7 ml (i.e. at least 7 cubic centimeters), in particular at least 8 ml, more in particular at least 10 ml or at least 11 ml. Additionally or alternatively, the volume of said main interior space 15 may not be larger than 40 ml, preferably not larger than 30 ml or not larger than 25 ml, in particular at most 20 ml or at most 18 ml, such as at most 15 ml or at most 12 ml.

Additionally or alternatively, the volume of the reservoir 19 may be at most 5 ml (i.e. at most 5 cubic centimeter) or at most 4 ml, in particular at most 3 ml, more in particular at most 2 ml, such as about 1 ml or about a half ml. Additionally or alternatively, the volume of the reservoir 19 may be at least 0.2 ml (i.e. at least 0.2 cubic centimeter), preferably at least 0.3 ml or at least 0.4 ml, such as about a half ml or about 1 ml.

By dimensioning the cup part 10 such that the main interior space 15, which may have substantially round cross-section, has, at its widest point, which preferably is located at or near an upper end of the cup part defining an upper end opening 16, a width or a diameter of at least 21 mm, in particular at least 25 mm, more in particular at least 30 mm, such as about 31 mm or about 33 mm, and/or wherein the main interior space 15 has, at its widest point, which preferably is located at or near an upper end of the cup part defining an upper end opening 16, a width of at most 55 mm, in particular at most 45 mm, more in particular at most 40 mm or at most 35 mm, such as about 34 mm or about 32 mm, it can be facilitated that the ectocervix 30 can fit into the main interior space 15 relatively well, for instance such as to facilitate that there may not be much room for a spermatozoon to get lost for mucus penetration, thereby increasing the chances that the spermatozoon reaches the os 31 of the cervix 3.

During use, the cup part 10, in particular a relatively small cup part 10, may more less huggingly engage the ectocervix 30 due to its relatively small dimensions, as for instance can be seen in FIG. 5. It can be advantageous that the ectocervix 30 can preferably fit relatively well within the main interior space 15 of the cup part 10, for instance to keep the distance between the os 31 of the cervix 3 and spermatozoon present within the cup part 10 relatively small. The sperm can be brought relatively close to the os 31 of the cervix 3 and the device 1 may therefore increase the amount of sperm that can enter the cervix 3, as a result of which it may facilitate increasing the odds of conception.

Although it may be advantageous that the ectocervix 30 can preferably fit relatively well within the main interior space 15 of the cup part 10, the cup part 10 may preferably be arranged such as to counteract that it may accidently block the os or so-called external orifice 31 of the cervix 3 in a manner in which it would unintentionally prevent sperm located within the main interior space 15 of the cup part 10 to flow towards said os 31 of the cervix 3. It is noted that, as can be seen relatively well in FIG. 2, the one or more indentations 12 in the side wall 11 of the cup part 10 may define one or more respective protrusions extending into the main interior space 15 of the cup part 10 that can form respective spacers which may facilitate that at least parts of the inner surface 115 of the side wall 11 of the cup part 10 may be kept spaced apart from the ectocervix 30 received within said main interior space 15.

By, additionally or alternatively, dimensioning the cup part 10 such that it has an outer width T118 or outer diameter T118, in particular at or near an upper end 116 or upper edge 17 of the cup part 10 defining an upper end opening 16, that is at least 21 mm, in particular at least 25 mm or at least 30 mm, more in particular at least 35 mm or at least 38 mm, such as about 40 mm, it can be facilitated that the cup part 10, in particular its upper end edge and/or sides of said cup part 10, can substantially contact the walls 42 of the vaginal canal 40 when the cup part 10 is moved through the vaginal canal 10 towards the cervix 3, thereby facilitating that relatively much of the ejaculate 2 present in said vaginal canal 40 can be collected and moved towards the cervix 3.

Moreover, the cup part 10 of the intravaginal conception assistance device 1 may comprise one or more airing holes 6, each designed as a through hole 6 extending through the side wall 11 of the cup part 10. In particular, the at least one airing hole 6 can be located at a distal end region of the cup part 10, more in particular near the distal end edge 17 of the cup part 10. The airing hole 6 may be for counteracting that, for example when reinverting the cup part 10 and/or when pulling out the cup part 10, a relatively low pressure arises inside the cup part 10, which relatively low pressure could be highly unwanted, for instance as it could impede reinverting the cup part 10 such as to fold it outside out again and/or make it a relatively painful experience, and/or as such relatively low pressure could impede removing the cup part 10 and/or could make the removal a relatively painful experience.

Although the airing holes 6 are here formed as relatively small, substantially round, through holes, one or multiple airing holes may have a different design in alternative embodiments. For example, at least one airing hole may be provided which is formed as a slit along the cup part. In particular, the cup part 10 could then be of such design that the at least one slit is substantially closed when the cup part 10 is pushed towards the ectocervix in its substantially inverted state, and that, when the cup part is substantially in its first state when it is being pulled out of the vagina 4, said at least one slit opens up to at least some extent.

In embodiments, the intravaginal conception assistance device 1 may be a disposable device 1 for single use. However, in alternative embodiments, it may be intended for multiple use. Thereto, the device 1 may be sterilisable, for example by means of boiling, using alcohol, using sterilizing tablets or the like, and/or by other suitable means or methods, such that it can be facilitated that for future use the device 1 will be substantially free of elements toxic to spermatozoa.

Further it is noted that the intravaginal conception assistance device 1, which has a substantially reversible cup part 10 being capable of being substantially folded inside out, may be part of a kit of parts, which further for instance may comprise semen friendly moisturizer.

Besides, it is noted that the semen friendly moisturizer may be a semen friendly lubricant providing for moisturizing action. It will be appreciated that the semen friendly lubricant and/or moisturizer may facilitate to make sexual intercourse more enjoyable, which may increase the chances of a female orgasm, and/or, for instance therefore, may further increase the chances of conception.

It is noted that for the purpose of clarity and a concise description features are described herein as part of the same or separate embodiments, however, it will be appreciated that the scope of the invention may include embodiments having combinations of all or some of the features described. For example, features disclosed in the context of the device will be considered to be disclosed also in the context of the kit of parts including said device, and will be considered to be disclosed also in a method in which such device is used, and vice versa.

Further, it is noted that the invention is not restricted to the embodiments described herein. It will be understood that many variants are possible.

For example, the cross-sectional shape of the cup part may for instance be substantially oval or elliptical instead of substantially circular or round, as is the case in the here shown embodiment.

As another example, it is noted that the handling element, which may for instance be a stem or other elongate handling element, does not necessarily be attached to a bottom region of the cup part, but may alternatively, or additionally, be attached to the cup part in one or more other suitable locations.

Furthermore, it is noted that although the device 1 in the shown embodiment has a cup part 10 which has a substantially cup-shaped side wall 11, which, in the initial or natural state of said cup part 10, has its outer surface 110 facing substantially outwardly and the inner surface 115 of the side wall facing substantially inwardly, the device 1 may alternatively be formed such that its cup part 10 is initially already in its substantially inverted state, e.g. a state substantially corresponding to the state shown in FIG. 3, in which the outer surface 110 of the substantially cup-shaped wall 11 of the, then substantially inverted, cup part 10 faces substantially inwardly and the inner surface 115 faces substantially outwardly.

Such and other variants will be apparent for the person skilled in the art and are considered to lie within the scope of the invention as formulated in the following claims.

The invention claimed is:

1. A method for collecting ejaculate from a wall of a vaginal canal and presenting the ejaculate near a cervix terminating the vaginal canal, the method comprising the steps of:
   inverting a resiliently deformable cup part of an intravaginal conception assistance device from a noninverted state to an inverted state;
   inserting the device into the vaginal canal;
   responsive to the step of inverting the cup part to the inverted state, presenting a ridge formed on a distal end of the device to a wall of the vaginal canal;
   pushing the cup part in the inverted state along the vaginal canal toward the cervix;
   responsive to the step of pushing the cup part, scraping ejaculate from the wall of the vaginal canal;
   reinverting the cup part from the inverted state to the noninverted state; and
   responsive to the step of reinverting, disposing the ridge radially inwardly so that the ridge no longer contacts the wall of the vaginal canal.

2. The method of claim 1, wherein the step of reinverting the cup part is accomplished by pulling a handle connected to a bottom portion of the cup part.

3. The method of claim 1, wherein the step of inverting the cup part is performed prior to the step of inserting the device into the vaginal canal.

4. A method for collecting ejaculate from a wall of a vaginal canal, the method comprising the steps of:
   elastically inverting a cup part of an intravaginal conception assisting device from a noninverted state to an inverted state;
   inserting the device into the vaginal canal with an apex of the inverted cup facing forward, a peripheral rim of the cup engaging a wall of the vaginal canal;
   pushing the cup part in the inverted state along the vaginal canal toward the cervix, thereby scraping ejaculate from the wall of the vaginal canal using a ridge portion of the rim facing outward;
   reinverting the cup part from the inverted state to the noninverted state, thereby bringing the ridge portion of the rim out of contact with the wall of the vaginal canal.

5. The method according to claim 4, wherein the ejaculate collected by the cup part is presented near the cervix terminating the vaginal canal.

6. The method according to claim 4, wherein the cup is elastically inverted by deformation of a cup wall, such that the rim is biased in an outward direction during pushing of the cup part through the vaginal canal, and is reinverted at an end of the vaginal canal near the cervix at least by pulling a handle portion connected at the apex of the cup.

7. The method of claim 4, wherein the vaginal canal has an end at which is formed an ectocervix, the ejaculate being at least partly received in said cup when reinverted, wherein the cup in the noninverted state is pushed against and/or over the ectocervix.

* * * * *